United States Patent [19]

Strongin et al.

[11] 3,965,351
[45] June 22, 1976

[54] DIFFERENTIAL AUGER SPECTROMETRY

[75] Inventors: Myron Strongin, Center Moriches; Matesh Narayan Varma, Shirley, both of N.Y.; Joshi Anne, St. Louis Park, Minn.

[73] Assignee: The United States of America as represented by the United States Energy Research and Development Administration, Washington, D.C.

[22] Filed: Oct. 30, 1974

[21] Appl. No.: 519,324

[52] U.S. Cl. .................................. 250/305; 250/307
[51] Int. Cl.² ............... G01N 23/04; G01N 23/227
[58] Field of Search ........... 250/305, 306, 307, 310, 250/311

[56] References Cited
UNITED STATES PATENTS

| | | | |
|---|---|---|---|
| 3,626,184 | 12/1971 | Crewe | 250/305 |
| 3,760,180 | 9/1973 | Weber | 250/305 |
| 3,909,610 | 9/1975 | Kokubo | 250/305 |

OTHER PUBLICATIONS

"Difference Auger Spectroscopy for Studying Small Quantities of Elements on Metallic Surfaces," Varma et al., Review of scientific Inst., vol. 44, No. 11, Nov. '73, pp. 1643–1645, 250–305.

*Primary Examiner*—Craig E. Church
*Attorney, Agent, or Firm*—Dean E. Carlson; Leonard Belkin; Cornell D. Cornish

[57] ABSTRACT

Differential Auger spectroscopy method for increasing the sensitivity of micro-Auger spectroanalysis of the surfaces of dilute alloys, by alternately periodically switching an electron beam back and forth between an impurity free reference sample and a test sample containing a trace impurity. The Auger electrons from the samples produce representative Auger spectrum signals which cancel to produce an Auger test sample signal corresponding to the amount of the impurity in the test samples.

5 Claims, 8 Drawing Figures

DIFFERENTIAL AUGER SPECTROMETRY

BACKGROUND OF THE INVENTION:

This invention was made in the course of, or under a contract with the United States Atomic Energy Commission.

In the field of metallurgy, Auger spectroscopy is an analytical technique used to identify the elemental composition of a sample surface. To this end, an incident electron beam having an energy (e.g., up to 3 keV) sufficient to knock an electron from an inner shell of an atom, is directed against the surface of the sample containing the trace element to be analyzed. The resultant vacancy is immediately filled by an electron from an outer shell, which gives up some energy to decay into the inner shell. The different in energy can be released in the form of a photon or by knocking out another electron from an outer shell called tha Auger electron. These electrons are then analyzed using a standard Auger spectrometer, such as the ones that are commerically available. The Auger spectrum thus obtained, comprises a signal containing peaks and valleys that give a quantitative measure of the elements present on the surface of the sample, as described in J. Appl. Phys. 40,314 (1969).

While the Auger spectrometer systems used heretofore have been successful, their sensitivities have varied from element to element and they have depended upon the Auger transition of interset. Morever, their sensitivities have often been markedly lower for dilute alloys because of the partial overlap of the peaks corresponding to the amount of the various elements present in the alloy. For example, the particular area of concern in the field of superconductors is the use of dilute alloys containing Nb and 1 percent zirconium. Accordingly, it is desirable to provide increased sensitivity of the Auger spectrometer system employed when working with dilute alloys. It is also advantageous to provide preferential cancellation of the peaks from the host elements of dilute alloys to provide greater senstivity for small amounts of impurity elements. Further, in the low energy region of the Auger spectrum where there is a large recorded slope in the dN(E)/dE curve, it is advantageous to remove the slope.

SUMMARY OF THE INVENTION:

This invention provides a method for increasing the sensitivity of Auger spectrometry by reducing overlapping Auger spectrum peaks and valley signals in micro-Auger spectroanalysis of the surface of dilute alloys containing at least two metal elements. To this end, the electron beam of a conventional Auger spectrometer is spatially modulated between first and second locii to produce first and second Auger spectrum signals having overlapping peaks and valleys corresponding to the various elements at the two locii when the beam is at the first and second locii respectively, the signal information being separately collected when the beam is at the respective locii, and the signal information is compared to provide a difference that reduces the overlapping signals.

In one embodiment, the electron beam is interacted with a pure reference sample of one host element at the first locus, and then alternately periodcially switched at 30Hz back and forth between the first locus and a second locus where there is positioned a sample of the host element containing a trace impurity, a trace being 4 percent or less of the host element. The two samples thus produce Auger electrons having characteristic Auger spectra for the host reference one element, and those Auger electrons produce signals that cancel. Thus, the Auger signal remaining from the test sample is free of the Auger signal corresponding to the host element.

It is an object of this invention, therefore, to provide an improved differential Auger spectrometer method and apparatus having increased sensitivity to trace elements in dilute alloys by cancelling the Auger signal corresponding to the host element in the dilute alloy.

The above and further novel features and objects of this invention will become apparent from the following detailed description of one embodiment when the description is read in connection with the accompanying drawings, and the novel features will be particularly pointed out in the appended claims.

BRIEF DESCRIPTION OF THE DRAWINGS:

In the drawings where like elements are referenced alike.

DESCRIPTION OF THE PREFERRED EMBODIMENT:

This invention is useful in Auger analysis of trace amounts of zirconium in the niobium host of a test sample forming a dilute alloy in which a minor amount of the zirconium is contained in the host sea formed by a major amount of niobium. However, this invention is useful in analyzing any alloy, although it is particularly useful in Auger analysis of dilute alloys that produce closely spaced or overlapping Auger peak signals, were increased sensitivity is required for one of the elements that produces one of the overlapping Auger signals.

It is known that standard Auger spectrometer apparatus is available for producing Auger electrons by using an electron beam that is centered by standard deflecting means against a test sample of a dilute alloy containing a major amount of a host element and a minor amount or a trace element. An electron gun for producing the required electron beam of electrons having the required energy to produce the characteristic Auger electrons desired is a standard well known item that is commerically available from Varian Associates, California, and Physical Electronics Industries, Minnesota. For example, electron energies of 3 keV are commerically available to produce characteristic Auger electrons for zirconium and niobium. One electron gun is shown and described in U.S. Pat. No. 3,831,101. Production of these Auger electrons by this type of an electron gun is based on the fact that all the electrons making up a particular beam have substantially identical momentum in substantially parallel trajectories, and the particles and mathematics of such electron guns are well known in the art. The invention hereinafter described utilizes an electron gun of this type in which the deflecting means is combined with a particular alternating wave oscillator source that spatially modulates the electron beam back and forth at a particular frequency between a test sample of the host element and the trace element whose characteristic Auger signals are overlapping, and the reference sample of the host element whose characteristic Auger signal is to be eliminated so as to increase the sensitivity of the spectrometer to the trace element. A description of the principles involved in this invention is given by the inventors in Rev. Sci. Instrum., Vol. 44, No. 11, Nov. 1973, page 1643.

Figure 1:
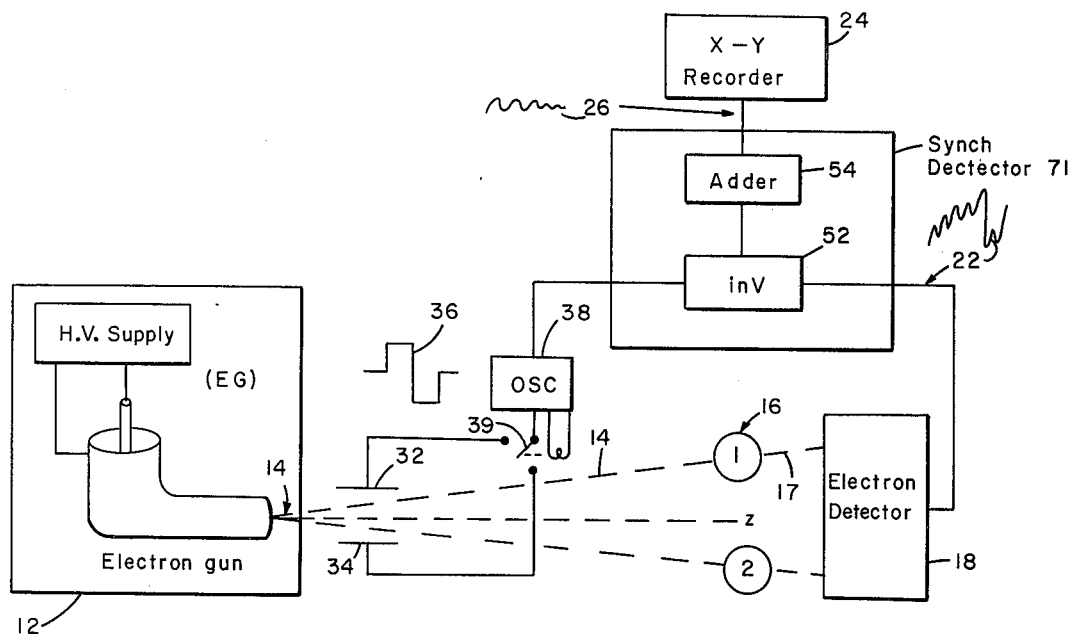
FIG. 1 is a partial schematic view of this invention.

In order to explain how the method and apparatus of this invention accomplish the function of spatially modulating the electron beam back and forth at the required frequency, reference is made to FIG. 1, which is a block diagram of an Auger spectrometer. The electron gun (EG) 12 provides a beam 14 that impinges on the sample surface of target 16 at a first locus 1 to produce secondary electrons comprising a characteristic spectrum of Auger electrons E whose trajectories in beam 17 are received in a standard detector 18 to produce a standard output signal 22 corresponding to the amount of the elements in the surface of the target 16. For example, an Auger spectrum signal 22 for Nb from detector 18 corresponds to the many different numbers of respective energies of Auger electrons E detected by the detector 18 from the target 16. This spectrum, which is conventional, can be displayed on a standard $x$ $y$ recorder 24. The peaks in the spectrum represent a predetermined number of Auger electrons E, and the valleys represent a lack of Auger electrons at energies on either side of the energy represented by the peak. For purposes of this invention the spectra of interest overlap by at least 20 percent and their peaks differ in amplitude by at least 20 percent.

In accordance with this invention, the electron beam 14 is switched back and forth by electrostatic deflection between locii 1 and 2 from a pure host reference sample to a test sample of 99.9 percent pure host element that contains a trace impurity element, which is defined herein as less than 4 atomic percent of the host, and which produces an overlapping Auger spectrum signal with the host, and the detected Auger spectrum signal 22 is inverted every time the electron beam is at locus 2, which inversion takes place in a time the electron beam takes to get back to the first locus 1, so that this locus 2 inverted signal cancels the host Auger spectrum signal when the electron beam is at locus 1. This cancellation, thus produces an output signal 26 that contains the remaining Auger spectrum, and by amplifying this remaining spectrum signal the amount of the trace element can be determined.

In order to explain how the method and apparatus of this invention accomplish the function of switching the electron beam while inverting the detector output signal in correspondence therewith, i.e., when the electron beam is at the second locus 2, reference is again made to FIG. 1, wherein is illustrated the equilibrium axis z, representing the path prior to alteration of an electron beam to undergo switching by electrostatic deflection.

Disposed along the z axis are a plurality of electrostatic deflecting plate pairs 32, each plate 34 of each pair, as is understood in the art, tending to electrostatically deflect the electron beam is some particular transverse plane, such as either the $x$ or $y$ planes perpendicular to each other and passing through the z axis, as is understood in the art. Each plate pair 32 consists of one plate for switching the beam in the $x$ or $y$ plane in one direction to locus 1 and one plate for switching the beam in the same plane in the opposite direction to locus 2. To this end, a square wave, alternating positive and negative voltage signal 36 is used to actuate one plate and then the other, so that positive signals 36 are applied to one plate, and equal amplitude negative signals are alternately periodically applied at a fixed frequency to the other plate.

One suitable signal is produced in a standard oscillator 38 by a standard square wave at a low frequency, which is defined herein as 60Hz or less. Switch 39 transmits the square wave alternately every half cycle, so that a square wave output 36 of equal amplitude and opposite polarity is alternately periodically applied respectively to the first and second plates 34 thirty times per second or less. As will be understood in more detail hereinafter, this frequency is low compared to standard detector operating frequencies. Also, the frequency matches the inverted and uninverted spectra in the proper phases, which closely correspond, as understood in more detail hereinafter.

When no electrostatic field is applied the electron beam is undeflected and the electrons have substantially equal energies, momenta and velocities along parallel closely bunched trajectories in the same direction. Should an electrostatic positive force be applied by one plate, a tranverse displacement of the electrons occurs equally in one direction since this displacement varies directly as voltage applied. Likewise, an equal and opposite polarity (negative) electrostatic force produces an equal and opposite transverse displacement.

In accordance with this invention, standard electron guns, in standard Auger spectrometers, having standard horizontal and vertical deflection plates are employed for deflecting and centering a standard continuous electron beam having a uniform energy and a diameter of no greater than 1mm on the Auger reference and test samples at first and second locii, and a standard oscillator is used for the deflection, which is timed for cancellation of the unwanted background signal. The oscillator is connected through a suitable switch to either the horizontal or vertical deflection plates in a standard electron gun, and it times the inversion of the Auger signal to occur when the electron beam is at the second locus, where the test sample is located. For purposes of this invention, the electron beam is defined as having gausian energy and velocity distributions, where the peak energy and velocity are no more than 20% greater than the minimum energy and velocity. Likewise 80% of the electrons have trajectories that are parallel within 0.20° of arc, and the electrons travel close to the z axis within a beam having a diameter of 1mm or less. Also, standard mechanical, or electrical switches 39, such as diodes, can be used that are operated automatically or manually.

In operation, the electron beam first produces Auger electrons E at the first locus 1 from a pure reference of one element in a host sample in a standard manner, while zero Auger electrons are produced at the second locus 2 from a pure test sample of the host element containing the trace impurity element. However, the latter sample is capable of producing an overlapping Auger spectrum with the host at the appropriate time. This appropriate time is a 60th of a second or less from the time the electrons impact the sample at locus 1, and to this end the beam is switched back and forth between the two locii at a constant low frequency, which matches the inversion of the Auger signal when the electron beam is at the second locus 2.

To coordinate the inversion of the Auger spectrum signals produced when the beam is at the second locus with the uninverted Auger spectrum signals when the beam is at the first locus, the same oscillator 38 for deflecting the electron beam is used to coordinate the inversion every half cycle of the oscillator in a standard inverter amplifier. Therefor, the inverter is responsive to the same oscillator to produce a synchronous inversion at the appropriate time every half cycle is an amplifier inverter 52 that amplifies both spectra with equal gain. Also, the inversion matches the uninverted spectrum signal from the first locus 1. Thereupon, when the inverted and uninverted spectrum signals 22 are added in adder 54 they cancel. Thus, when the background spectrum of the pure reference host element is cancelled, the remaining Auger spectrum signal 26 corresponding to the trace element at the second locus is transported to and received by the $x - y$ recorder 24 which records the signal 26 without any overlap with signal 22.

Figure 1A:
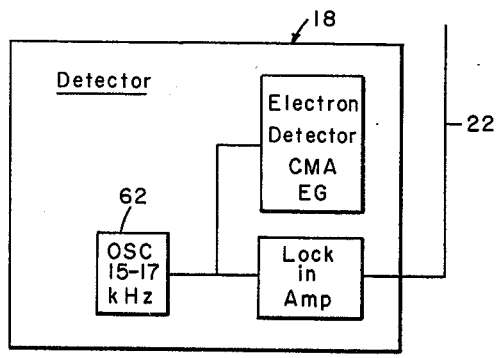
FIG. 1a is a detailed block diagram of the detector of FIG. 1.
Figure 1B:
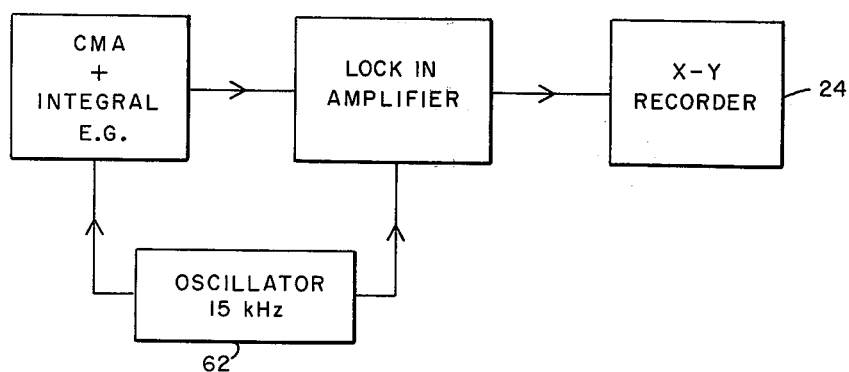
FIG. 1b is a block diagram of a standard Auger spectrometer.
Figure 2:
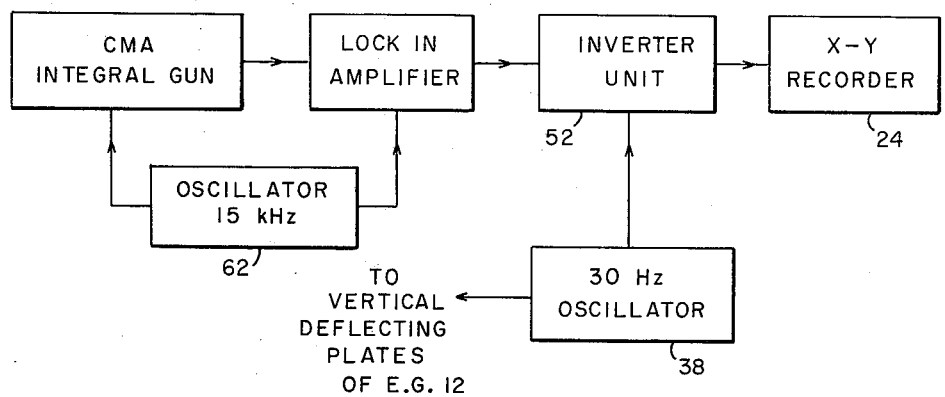
FIG. 2 is a partial schematic block diagram of the differential Auger spectrometer of this invention.

As is understood in the art, this invention utilizes a standard Auger spectrometer in which the detector and electron beam are combined. To this end, reference is made to FIG. 1a, which shows that the detector has its own oscillator 62 for modulating the detector output and demodulating the same at a fast frequency relative to the electron beam switching frequency. A block diagram of the standard system without the inverter and low frequency oscillator of this invention are shown in FIG. 1b, while a block diagram of this invention is whown in FIG. 2. As seen in FIG. 2, this invention adds an inverter that is connected and synchronized with the electron beam position by the oscillator for switching the electron beam back and forth between the described two locii.

In order to combine the detector and electron gun in a single structure the characteristic Auger electrons E are focused in a standard cylindrical mirror analyzer (CMA) shown in FIG.'s 1b and 2, and a small portion of these Auger electrons E are then passed through a co-axial cylinder that acts as an energy filter for the desired characteristic Auger electrons of the elements in the electron beam target 16. By varying the voltage on these cylinders in a known manner the electron energy distribution of the characteristic Auger electrons E is obtained as a spectrum signal output. This signal output is then amplified in an electron multiplier, and the resulting signal is differentiated by using a lock-in detector amplifier shown in FIG.'s 1b and 2 to attain a characteristic Auger spectrum signal, which corresponds to $dN(E)/dE$. AC frequencies of the order of 15–17 kHz are superimposed on the co-axial cylinders for this purpose, and the modulator frequency of the electron beam in accordance with this invention must be <1 percent of the oscillator frequency used for the Auger energy filter.

Figure 3:
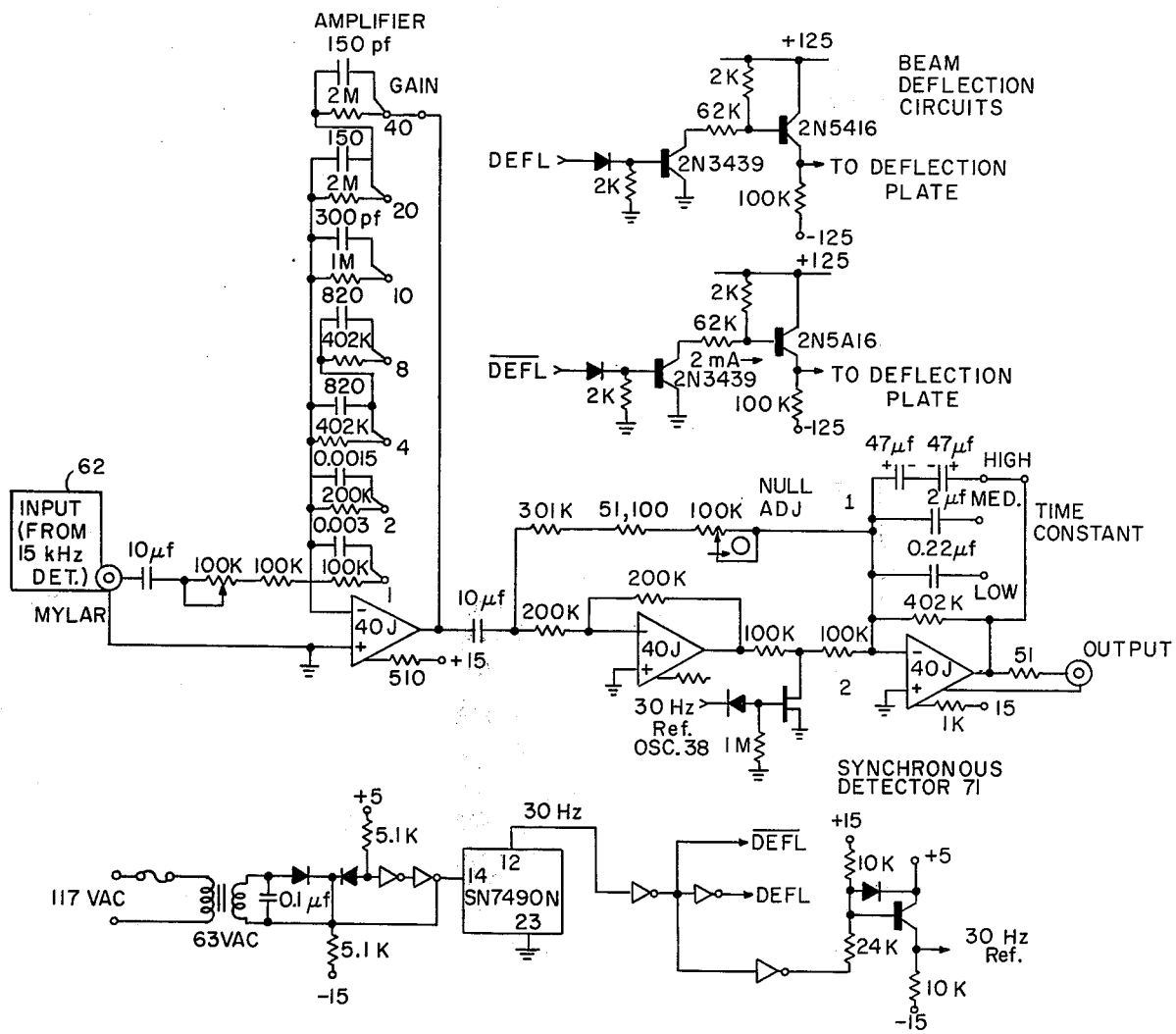
FIG. 3 is a detailed circuit diagram of the synchronous detector and deflection driver for the difference Auger spectrometer of FIG. 2.

Referring to FIG. 3, a detailed circuit diagram is provided of one embodiment which provides a synchronous detector 71 and deflector in a difference Auger spectrometer so that the Auger signal from the reference host sample is inverted to cancel the Auger signal from the test sample containing the host and the trace element to be detected with increasing sensitivity when the host and trace elements produce overlapping Auger signls. The following are examples of this invention:

EXAMPLE I

In one example, the electron beam at the two locii is of substantially equal intensity, and the reference sample is at the first locus one, while an identical test sample is positioned at the second locus. In this case one gets substantially identical outputs from both locii and when one of the outputs is inverted, the inverted output substantially cancels the first output. Thus, a zero output is achieved, as the two spectra cancel each other out completely. However, if the first sample and the second sample at the two locii are not identical — for example if in sample 1 is pure niobium and sample two is Nb - 1% Zr — then in the output of the inverter unit one would observe the spectrum characteristic of zirconium, while the approximately equal niobium peaks would cancel each other. This is significant since the difficulty in a standard Auger spectrum arises due to the closeness and overlap of the Auger peaks from niobium and zirconium, thus reducing the apparent sensitivity for the zirconium peaks.

It is important that the difference signal be observed over a time that is large compared to the scanning time of a particular peak and for this reason a variable time constant is provided in the inverted unit. A low practical switching frequency is chosen so that it provides enough time to sample the surface of the material relative to the high frequency modulating frequency for the detector. Additionally, the gain for the detector is variable to increase the amplitude of the Auger spectrum signal for the detected trace element in the test sample.

EXAMPLE II

The steps of example I are repeated. A square wave voltage of +125 to −125 V at 30Hz was applied every half cycle to one then the other of two vertical deflection plates of a standard electron gun of a standard Auger spectrometer, while the horizontal deflection plate voltage of the electron gun was held fixed. This deflected the electron beam an amount equal to 0.8 mm (about 1/32 inch) so that the beam appeared as split into two respective spots on the test and reference samples, the spots and samples being separated by a distance of about 0.8 mm.

The effect of deflecting the electron beam in opposite directions in a cycle is that a signal is produced at the output of the lock-in amplifier, so that in one half of the cycle one observes the uninverted signal when the electron beam is at the first locus 1 and an inverted signal in observed when the electron beam is at the second locus. The respective signals are then added to cancel the background overlapping spectrum signal.

With the described conventional equipment the electron beam cross-sections, referred to as spots at the specific locii, were separated symmetrically about the central $z$ axis but the intensities in the two positions was not the same. As a result, when the samples were identical (or both spots were on the same sample) the output signals from the synchronous inverter did not cancel completely from the two spots. Thus, when the beam was deflected between two spots on a degassed Nb foil, the final signal from the inverter contained small peaks, as shown in FIG. 4(b). FIG. 4(a) shows the difference Auger spectrum when the beam was deflected between Nb and vacuum. From these two spectra it appears that there was about 90% cancellation. This, however, can be improved if the intensities of the two beams are made equal.

Since the separation between the two beams is extremely small, slight tipping of the samples relative to each other or the beam, if any, causes only neglible asymmetry with respect to the analyzer, Other factors that can influence the results are small differences in work function and chemical shifts resulting from composition changes.

The electron beam energy was uniformly 500 keV up to 3 keV, and in this example 1.5 keV was typical. The advantage of the lower energy is that it produces less damage and/or chemical change in the test sample surface. Thus, this invention has utility where the use of other higher energy systems is precluded. It was found that an electron beam energy of 500 eV was the lower limit for producing Aguer electrons from Zirconium and Niobium, and that electron beam energies higher than 1.5 keV could damage the surface of the test or reference samples.

EXAMPLE III

Figure 5:
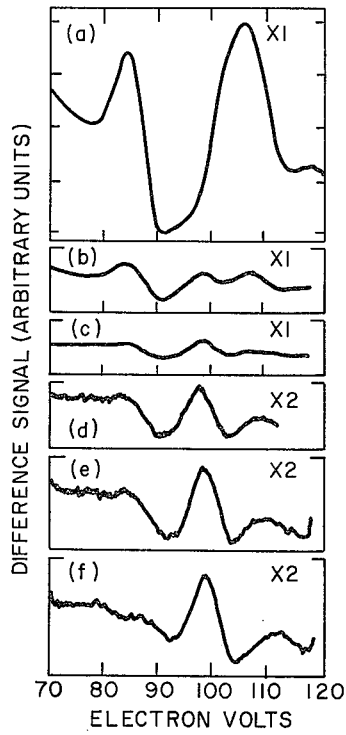
FIG. 5 is a graphic illustration of the difference signal produced with the apparatus of FIG. 3, with the beam switched between Nb and Nb - 1 percent Zr samples: (a) before sputtering, (b) - 1 min sputtering, (c) - 2 min sputtering, (e) - 3 min sputtering, (f) - 8 min sputtering.

The steps of Example II were repeated where one sample at the second locus was 99.9% pure Nb - 1% Zr foil of 0.25 mm thickness, and the other sample at the first locus was 99.9% pure niobium foil of 0.025 mm thickness. The samples were separated by a distance < 0.8 mm from each other. The difference Auger spectrum for this example is shown in FIG. 5(a). A large peak was observed at 93 eV corresponding to the zirconium.

EXAMPLE IV

Figure 6:
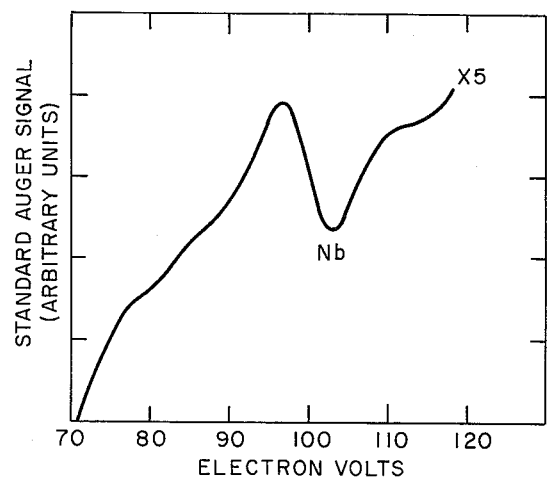
FIG. 6 is a graphic illustration of a standard Auger spectrum of Nb - 1 percent Zr alloy after sputtering for 3 min.

The steps of Example III were repeated with a Nb - 1% Zr dilute alloy sample, wherein the Zr segregated to the surface when the alloy was heated to the 1000°–1200°C range. When the surface atoms were removed by ion bombardment, the peak height of Zr diminished. The spectra obtained after 1, 2, 3, and 8 min. sputtering are shown in FIGS. 5(b)–5(f). It can be seen from these spectra that the zirconium peak is still observable after 8 min. sputtering. This spectrum, shown in FIG. 5(f), is also similar to one of long-time sputtering. This also indicated that the detection capability of this technique is lower than 1% Zr in Nb - 1% Zr. In arriving at this estimate it was assumed that Nb and Zr are sputter removed at about the same rate in the Nb - Zr alloy. In comparison, in FIG. 6, a spectrum obtained from Nb - 1% Zr after sputtering for 3 min. did not indicate a zirconium peak when standard Auger technique was used. A rough estimate shows that zirconium contents of about 4% can be identified by the standard technique. Thus, the new technique of this invention provides a several fold increase in sensitivity in identifying small quantities of solute elements and promises to be better if the electron beam can be improved.

EXAMPLE V

The steps of Example IV were repeated with a test sample containing Nb - 1% Zr foil 0.25 mm thick at the first locus and a 99.9% pure Nb foil 0.025 thick and lacking zirconium at the second locus.

The Auger electrons E were transmitted to standard Auger spectrometer systems when the beam was at the respective locii for collecting and processing the Auger electrons into characteristic Auger spectrum signals corresponding to the amounts of the host and trace elements present in the test and reference samples. To this end the Auger electrons were analyzed in a cylindrical mirror analyzer, and a small portion of the Auger electrons were then passed through a co-axial cylinder that acted as an energy filter. by varying the voltage on these cylinders the electron energy distribution functions were obtained, amplified and differentiated by using a lock-in detector to attain dN (E)/dE. AC frequencies of the order of 15–17 kHz were superimposed on the co-axial cylinders for this purpose.

By synchronizing the above-mentioned amplification with the spatial modulation of the beam oscillation so that the amplified signal was inverted when the beam was at one locus, and not inverted when the beam was at the other locus, it was possible to cancel the Auger signal from the test sample corresponding to the host element. Thus, this cancelled Auger signal did not overlap the Auger signal from the trace element, and the spectrometer thus had an increased sensitivity to the trace element.

Figure 4:
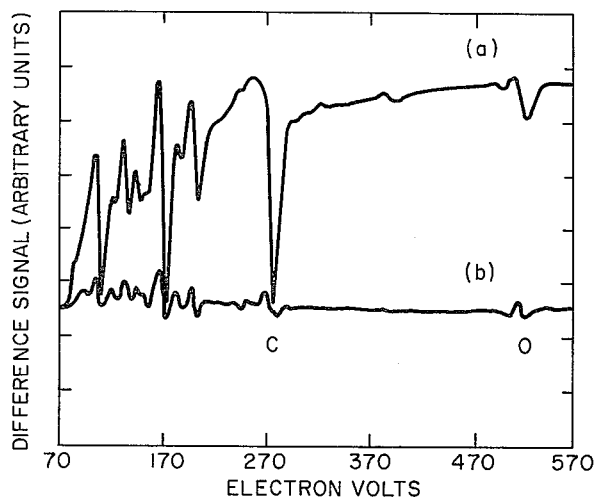
FIG. 4 is a graphic illustration of the difference Auger spectrum produced by the apparatus of FIG. 3.

Two difference Auger spectrums are shown in FIG. 4. Curve (a) represents the Auger specturm represented by dN(E)/dE when the electron beam was switched back and forth between an Nb reference sample at a first locus and a vacuum at a second locus. On the other hand, when the electron beam was switched between a Nb test sample and/or Nb reference sample, as shown in curve (b), the Nb Auger peak C was substantially cancelled.

EXAMPLE VI

The steps of Example V are repeated. It is possible in standard electron guns in standard Auger spectrometers to deflect the electron beam back and forth in the horizontal or vertical position by applying voltages to either the horizontal or vertical deflecting plates. In the example of this invention described herein, a constant square wave, ac, signal input amplitude was applied to the vertical deflecting plates, while the horizontal deflecting plates were held at a constant voltage by clamping the same to a fixed voltage source. This spatially modulated the beam between first and second locii by deflecting the beam alternately periodically to switch it back and forth between the reference and trace impurity containing samples.

The effect of spatially modulating the electron beam back and forth by switching it at a particular, timed, low frequency, is to produce an output in a standard Auger detector signal system, so that in one half of the cycle one observes the signal when the beam is at a first locus and in the other half of the cycle a signal when the beam is at a second locus. Then, by feeding the signals to a synchronous detector that operates at the switching frequency of the deflecting plates, the detector signal when the electron beam is at the first locus, is passed as is, and the signal from the detector when the electron beam is at the second locus is inverted by the inverter circuit shown in FIG. 3 and is added to the uninverted signal, so that the output provides the difference in signal from the two systems when the electron beam is at the two locii respectively. This difference signal when plotted on a standard $x - y$ recorder as a function of Auger electron energy from the two locii respectively, gives a difference Auger spectrum.

EXAMPLE VII

The steps of Example VI are repeated using the circuit of FIG. 3. In this example, a 60Hz sine wave from a suitable oscillator source was converted to a 30Hz square wave having equal amplitude, opposite polarity ½ cycles alternately periodically at a fixed frequency in each half cycle, and each half cycle the square wave was supplied to one and then the other of two deflection plates of a standard electron gun in a standard Auger spectrometer.

The same 30Hz square wave was supplied as a reference to the synchronous inverter of FIG. 3 to time the inversion of the amplified signal from the standard Auger electron detector when the electron beam was at the second locus. The 40J amplifiers applied equal gain to the inverted and uninverted signals when the electron beam was at the respective first and second locii. The inverted signal matched the uninverted signal.

A Nb reference sample and a Nb - 1% Zr test sample were located at the respective locii. When the inverted and uninverted signals were added to cancel the Nb background, the remaining spectra recorded on the $x - y$ recorder showed an Auger spectrum corresponding to 1% Zr at the surface of the test sample. Then the gain was turned up in the preamplifier for the inverter to more clearly show the Auger spectrum for the 1% Zr trace in the Nb host of the test sample.

This invention has the advantage of increasing the sensitivity of micro-Auger spectronaalysis in the Auger spectrometer for determining the quantity of trace amounts of impurity in a host element. To this end, this invention modifies existing apparatus, and provides an improved method that is timed with the Auger detection to switch the electron beam back and forth at a particular fixed frquency between test and reference samples. For purposes of this invention micro-Auger analysis is defined as being for dilute alloys, comprising a host and a trace impurity less than 4 atomic percent of the host element.

What is claimed is:

1. The method of controlling micro-Auger spectroanalysis of the surfaces of dilute alloys containing at least two metal elements, comprising:
    a. spatially modulating a uniform low energy electron beam having a diameter of at least up to 1mm of parallel electrons in an Auger spectrometer between first and second locii at a first frequency to produce Auger electrons corresponding to the elements at the locii;
    b. collecting the Auger electrons produced when said beam is at said first locus;
    c. separately collecting the Auger electrons when said beam is at said second locus; and
    d. comparing the spectra of the Auger electrons collected for obtaining the difference therebetween, a pure reference sample being situated at said first locus and a sample of a dilute alloy containing a trace impurity less than 4 atomic percent being situated at the other of said locii so that said difference can be used to negate the Auger electron component from the locus corresponding to the pure reference sample Auger electrons.

2. The method of 1 wherein the electron beam is deflected to interact with the pure reference sample; the beam is deflected to interact the beam with the sample containing the trace impurity at the surface thereof; the beam is alternately and periodically switched back and forth at a fixed low frequency of up to only 60Hz between the reference and impurity containing samples; the Auger electron reaction products resulting from the interactions are detected so as to produce two respective signals corresponding to the Auger electron reaction product numbers of the respective reaction products resulting from the interaction, and the two signals are compared in timed relation with the electron beam switching to produce a difference signal corresponding substantially linearly with the difference between the respective particle numbers detected for negating the signal component from the second locus corresponding to the pure reference sample Auger electrons, the respective particle numbers detected corresponding to specific electron energies in accordance with Auger electrons produced by the various elements in said samples.

3. The method of claim 2 in which the electron beam is switched back and forth respectively between the reference and trace impurity containing samples at 30Hz.

4. The method of claim 3 in which the respective signals correspond to two elements, the signals for one element are electronically cancelled in timed sequence with said 30Hz so that the final output is the Auger spectra for the other element and is, therefore, sensitive to small differences in composition between the samples relative to the other element.

5. The method of claim 3 in which the electron beam is produced by an electron gun having a vertical deflecting plate connected to a 30Hz oscillator through a switch for switching the beam back and forth between the samples at 30Hz.

* * * * *